(12) United States Patent
Quinn

(10) Patent No.: US 6,319,278 B1
(45) Date of Patent: Nov. 20, 2001

(54) LOW PROFILE DEVICE FOR THE TREATMENT OF VASCULAR ABNORMALITIES

(76) Inventor: Stephen F. Quinn, 3365 Bardell Ave., Eugene, OR (US) 97401

(*) Notice: Subject to any disclaimer, the term of this patent is extended or adjusted under 35 U.S.C. 154(b) by 0 days.

(21) Appl. No.: 09/518,014

(22) Filed: Mar. 3, 2000

(51) Int. Cl.⁷ ........................................................ A61F 2/06
(52) U.S. Cl. ........................................................ 623/1.13
(58) Field of Search ........................... 623/1.13, 1.1, 623/1.16, 1.12; 606/198, 191, 195

(56) References Cited

U.S. PATENT DOCUMENTS

| | | |
|---|---|---|
| 5,282,824 * | 2/1994 | Gianturco ............................ 623/1.13 |
| 5,443,496 | 8/1995 | Schwartz et al. . |
| 5,562,697 | 10/1996 | Christiansen . |
| 5,591,195 * | 1/1997 | Taheri et al. ........................ 623/1.13 |
| 5,693,084 | 12/1997 | Chuter . |
| 5,851,228 * | 12/1998 | Pinheiro .............................. 623/1.13 |

* cited by examiner

Primary Examiner—Kevin Truong
(74) Attorney, Agent, or Firm—Robert E. Howard

(57) ABSTRACT

A low profile stent graft for treatment of vascular abnormalities such as aneurysms. The endoskeleton of the stent graft has first and second self-expandable stents. The stents are spaced apart and connected together by at least one, and preferably three, flexible strut members. A tubular graft is placed around the endoskeleton while the stents are in a partially compressed state, and attached to the stents. A bifurcated configuration is disclosed that can be employed where the stent graft is to be used for repair of an aneurysm of the abdominal aorta.

11 Claims, 5 Drawing Sheets

LOW PROFILE DEVICE FOR THE TREATMENT OF VASCULAR ABNORMALITIES

BACKGROUND OF THE INVENTION

This invention relates to a low profile device for treatment of vascular abnormalities, such as the repair of aneurysms.

In the past, treatment of aneurysms involved an open surgical procedure which exposed the affected lumen and bypassing the aneurysm with an artificial tubular graft.

More recently stent grafts have been employed as a minimally invasive alternative to traditional graft bypass surgery. There are a number of stent graft designs that have been tried. Current designs are limited to use with patients having large vessels because of the large size of the delivery systems. Such large sizes require surgical exposure of the vascular system and in smaller patients, often females, such stent grafts are simply too large to use at all. In addition, such larger stent graft designs can be difficult to position and may cause damage to the blood vessels.

SUMMARY OF THE INVENTION

It is an object of the present invention to provide a stent graft design that has a low cross sectional profile that can be delivered percutaneously and used in patients with small and tortuous vessels.

It is a further object to provide a stent graft that is highly flexible.

It is a still further object to provide a stent graft that is simple and inexpensive to construct.

These and other objects are achieved by providing a stent graft that has a minimal metallic endoskeleton that holds the graft material in place until secondary deployment of additional stents. Such a minimal metallic endoskeleton allows the delivery system to have a lower cross-sectional profile than conventional stent grafts.

The endoskeleton of the stent graft of this invention has a first self expandable metallic stent located at the distal end thereof and a second self expandable metallic stent located at the proximal end thereof. At least one flexible longitudinal strut member extends between and is connected to the first and second stents. The strut member can have a fixed length or can be a compound strut comprised of two or more strut sections that are fastened together in a manner that allows a sliding motion between the strut sections so that the compound strut can be elongated by applying traction to the proximal stent.

The endoskeleton of the stent graft of this invention may be bifurcated for use with aneurysms of the abdominal aorta.

The endoskeleton of the stent graft of this invention is inserted into a tube of a graft material and the tube attached to the first and second stents. In the case of the bifurcated system, the graft material is also connected to the third contralateral stent.

DESCRIPTION OF PREFERRED EMBODIMENTS

Figure 1:
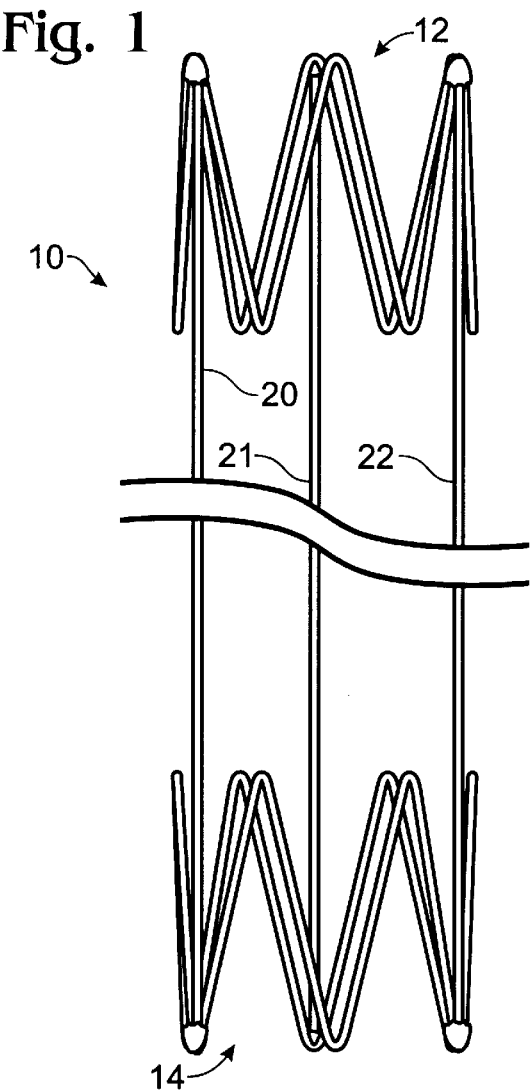
FIG. 1 is a plan view of a straight tubular form of the endoskeleton of the stent graft of the present invention.

The endoskeleton 10 of the straight tubular form of stent graft 30 is illustrated in FIG. 1.

Figure 2:
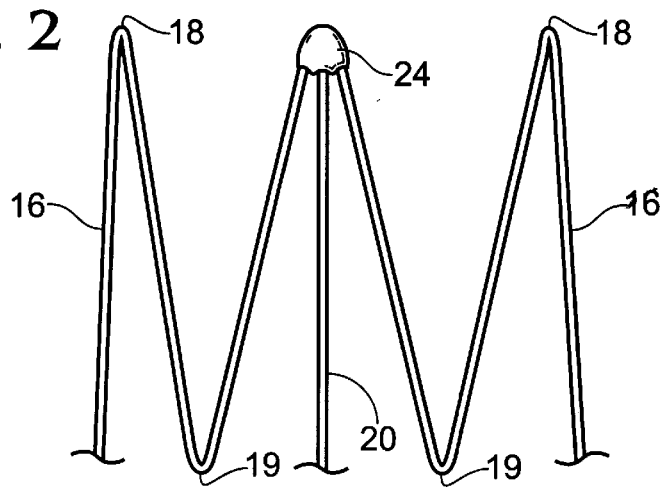
FIG. 2 is a plan view of a portion of a stent used in the invention.

Endoskeleton 10 is comprised of a first stent 12 and a second stent 14. Stents 12 and 14 are identical in construction, each being a cylindrical spring assembly made from a single piece of fine gauge stainless steel spring wire or nitinol having a diameter of about 0.4 to 0.5 mm that is bent into a sinusoidal configuration comprised of a plurality of arms 16 and outer and inner elbows 18 and 19, respectively, as best seen in FIG. 2. Elbows 18 and 19 are illustrated as being simple arches, but other elbow configurations, such as a recurved arch or aperatured arch may be used.

Struts 20, 21, and 22 extend between first and second stents 12 and 14, as shown. Struts 20-22 are constructed of fine gauge stainless steel spring wire or nitinol having a diameter of about 0.3 to 0.6 mm. Struts 20-22 are attached to stents 12 and 14 in any suitable manner, such as soldering to outer elbows 18 at solder joint 24; they may, alternatively be attached by bending, or cut from a single piece of metal. The struts are substantially evenly spaced apart around cylindrical stents 12 and 14.

Although three struts are preferred, a single strut may be used. More than three struts may also be used, but the number used should not be such that the flexibility of the stent graft is compromised.

Figure 3:
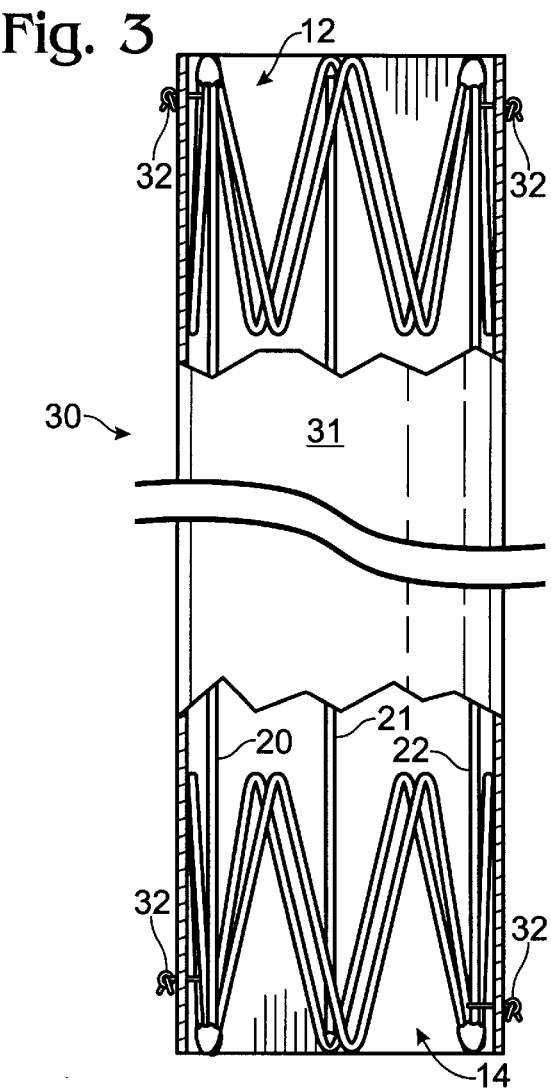
FIG. 3 is a plan view, partially in section, of the straight tubular form of the endoskeleton attached to the inside a tubular graft.

A straight tubular stent graft 30 is formed by compressing stents 12 and 14 and inserting endoskeleton 10 into elongated cylindrical graft tube 31, as best seen in FIG. 3. The graft tube 31 is attached to stents 12 and 14 by sutures 32 passed through graft 31 and outer elbows 18.

Graft tube 31 may be formed of any conventional graft material which is known to be substantially biologically inert, non-biodegradable, and durable. A suitable such graft material is polytetrafluoroethylene ("PTFE") sold under the trademark "IMPRA" by Bard of Tempe, Arizona. The diameter of the graft tube 31 can be between about 6 and about 40 mm in diameter and between about 1.5 and about 400 mm in length.

Figure 4:
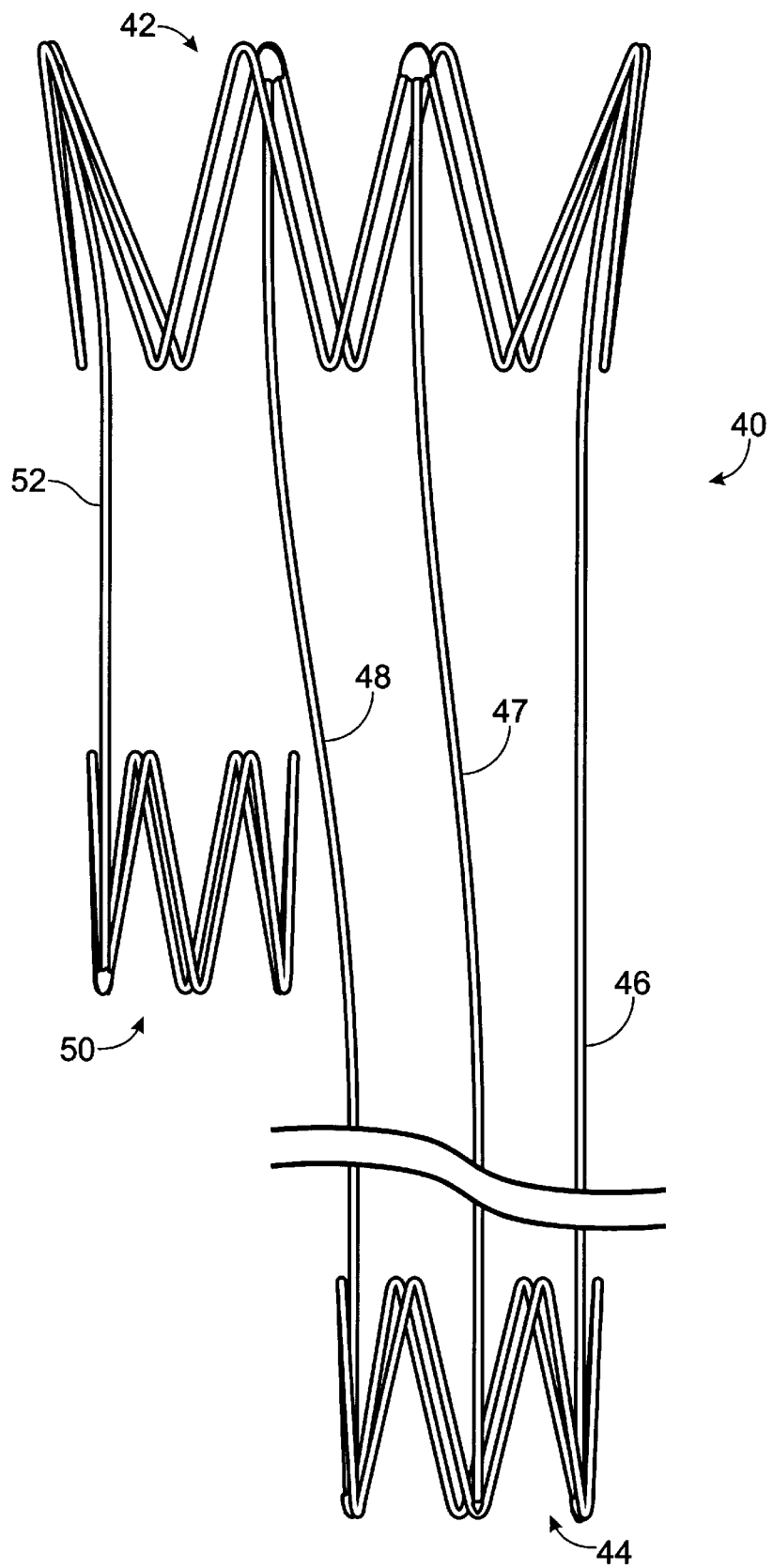
FIG. 4 is a plan view of a bifurcated form of the endoskeleton of the stent graft of the present invention.

The endoskeleton 40 of a bifurcated form of stent graft 60 of this invention is illustrated in FIG. 4. Endoskeleton 40 is comprised of a first stent 42 and a second stent 44 having struts 46, 47, and 48 extending therebetween and attached thereto in the same manner as for the straight tubular form 10 discussed above. Stents 42 and 44 are cylindrical spring assemblies of the same configuration and material as discussed above, except that stent 42 has approximately twice the diameter of stent 44. Stent 50 is attached to stent 42 by means of a single strut 52.

Figure 5:
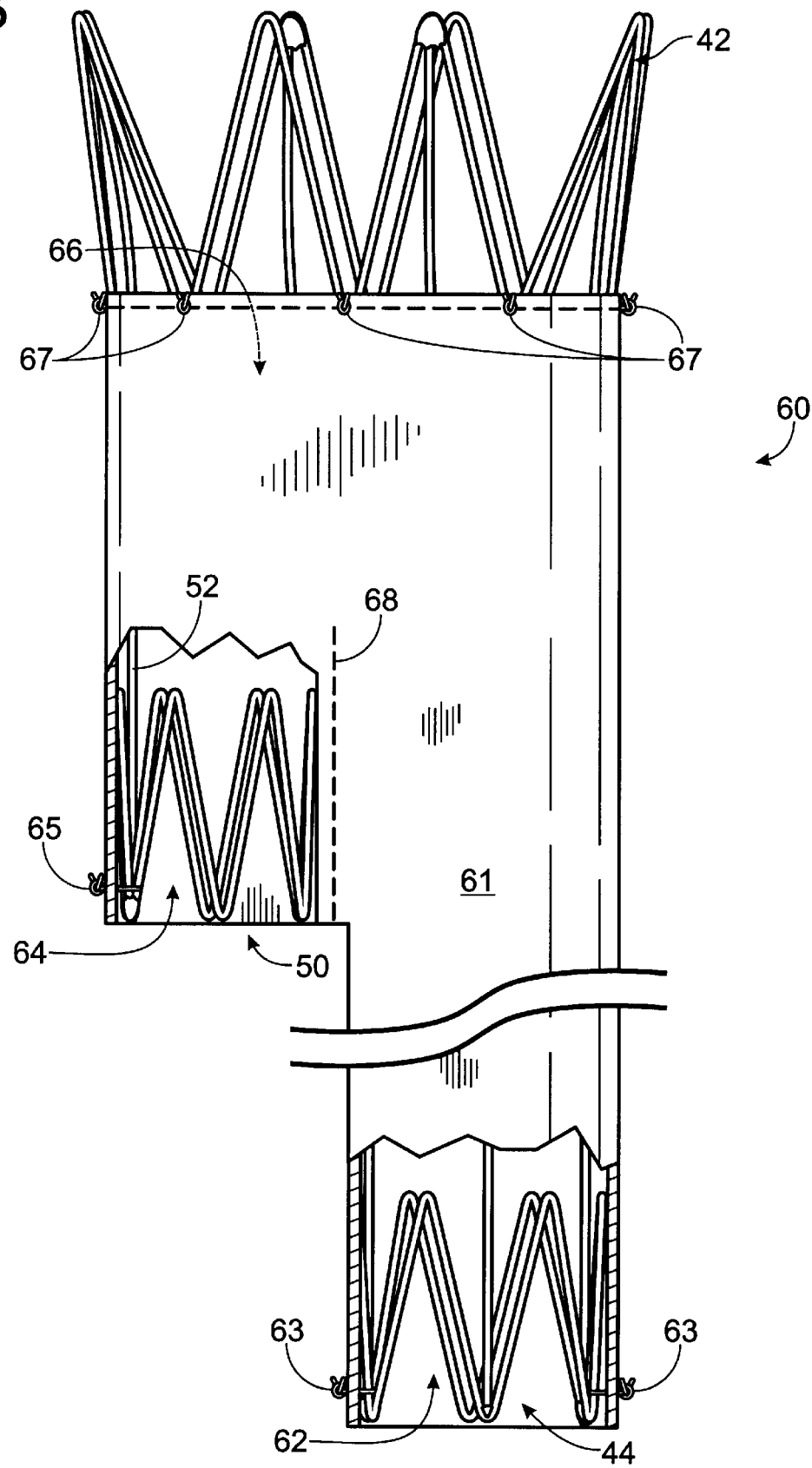
FIG. 5 is a plan view, partially in section, of the bifurcated form of the endoskeleton attached to the inside of a tubular graft.

Bifurcated stent graft 60 is formed by positioning a partially compressed bifurcated endoskeleton 40 inside a bifurcated tubular graft 61 as shown in FIG. 5. Graft 61 is formed of the same material as graft 31.

Stent 44 is located inside, and adjacent the end of, channel 62 and sewn to graft 61 by sutures 63, only two of which are shown. Stent 44 is in a partially compressed state so that an outward force is applied to the inner side of channel 62.

Stent 50 is located inside, and adjacent the end of, channel 64 and sewn to graft 61 by sutures 65, only two of which are shown. Stent 50 is in a partially compressed state so that an outward force is applied to the inner side of channel 64.

Stent 42 extends outwardly from the end of channel 66 and is sewn to graft 61 by sutures 67, only two of which are shown. Being in a partially compressed state at its inner end, stent 42 exerts an outward force on the inner side of channel 66.

Stent 42 is not covered by graft material 61 to allow placement of the stent graft 60 across critical branch vessels without causing occlusion, the blood flowing through the open structure of the uncovered stent. This is especially true in the abdominal aorta where the renal arteries are just above the level of the aneurysms. An uncovered stent 42 can be placed safely across the origins of the renal arteries and still allow a fixation site for the stent graft 60.

Graft material 61 is configured to wrap around stent 50 and is sewn along stitch line 68 to form channel 64. There is no communication between channel 62 and channel 64 along the stitch line 68, but both channels 62 and 64 communicate with channel 66.

Bifurcated stent graft 60 is used to repair aneurysms of the abdominal aorta which typically occur where the aorta branches into smaller (iliac) arteries. Bifurcated stent graft 60 can be used in conjunction with the straight tubular stent graft 30 described above by inserting straight tubular stent graft 30 into channel 64 of bifurcated stent graft 60 and sewing it into place. The end of bifurcated stent graft 60 containing channel 66 is located in the aorta with channel 50 (extended by insertion of a stent graft 30) and channel 62 being located in the adjacent iliac arteries.

Figure 6:
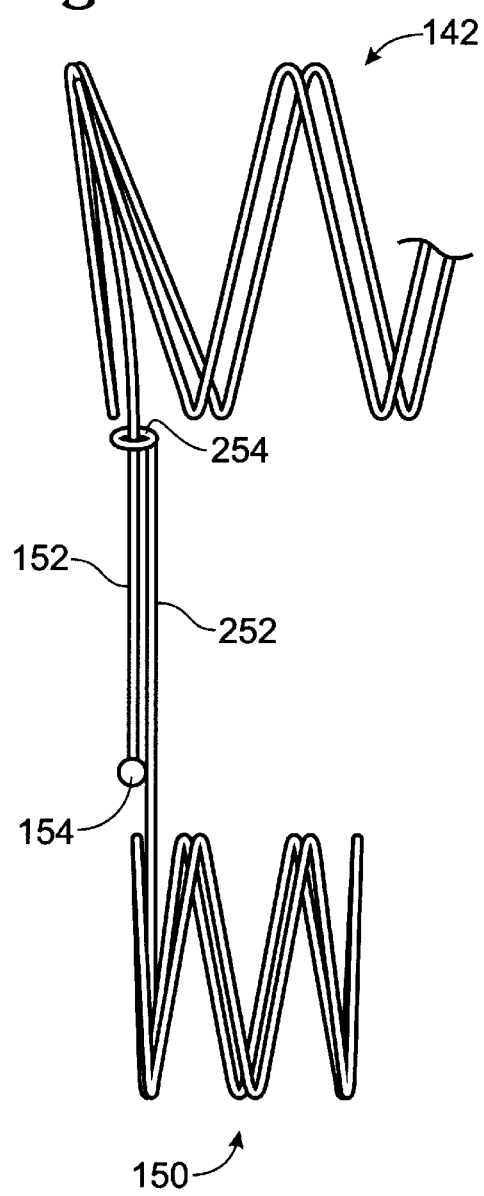
FIG. 6 is a partial plan view of the bifurcated stent attached to a two component strut to permit sliding elongation, shown in its collapsed condition.
Figure 7:
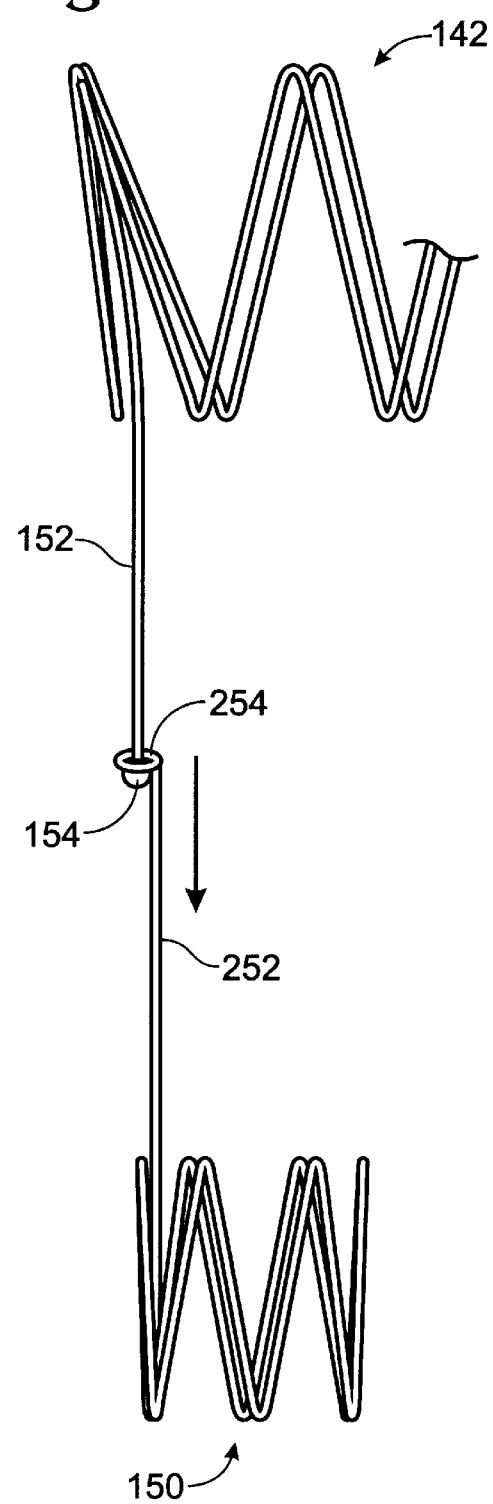
FIG. 7 is a partial plan view of the strut of FIG. 6 shown in its extended condition.

A variation of the endoskeleton of bifurcated stent graft 60 is shown in FIGS. 6 and 7. In this variation, single strut 52 of FIG. 4 is replaced by a two component strut comprised of fixed strut 152 and sliding strut 252. Fixed strut 152 is attached to stint 142 and sliding strut 252 is attached to stint 150, the reference numbers of the components in FIGS. 6 and 7 common to those in FIG. 4 being the same but increased by 100 or, in the case of the sliding strut, by 200.

Sliding strut 252 has a ring 254 attached at its outer end. Ring 254 fits over fixed strut 142 in sliding relationship. In FIG. 6 sliding strut 252 is shown in its unextended (collapsed) configuration. In FIG. 7 sliding strut 252 is shown in its extended configuration. Cap 154 attached to the outer end of fixed strut 152 prevents passage of ring 254 thereover.

Figure 8:
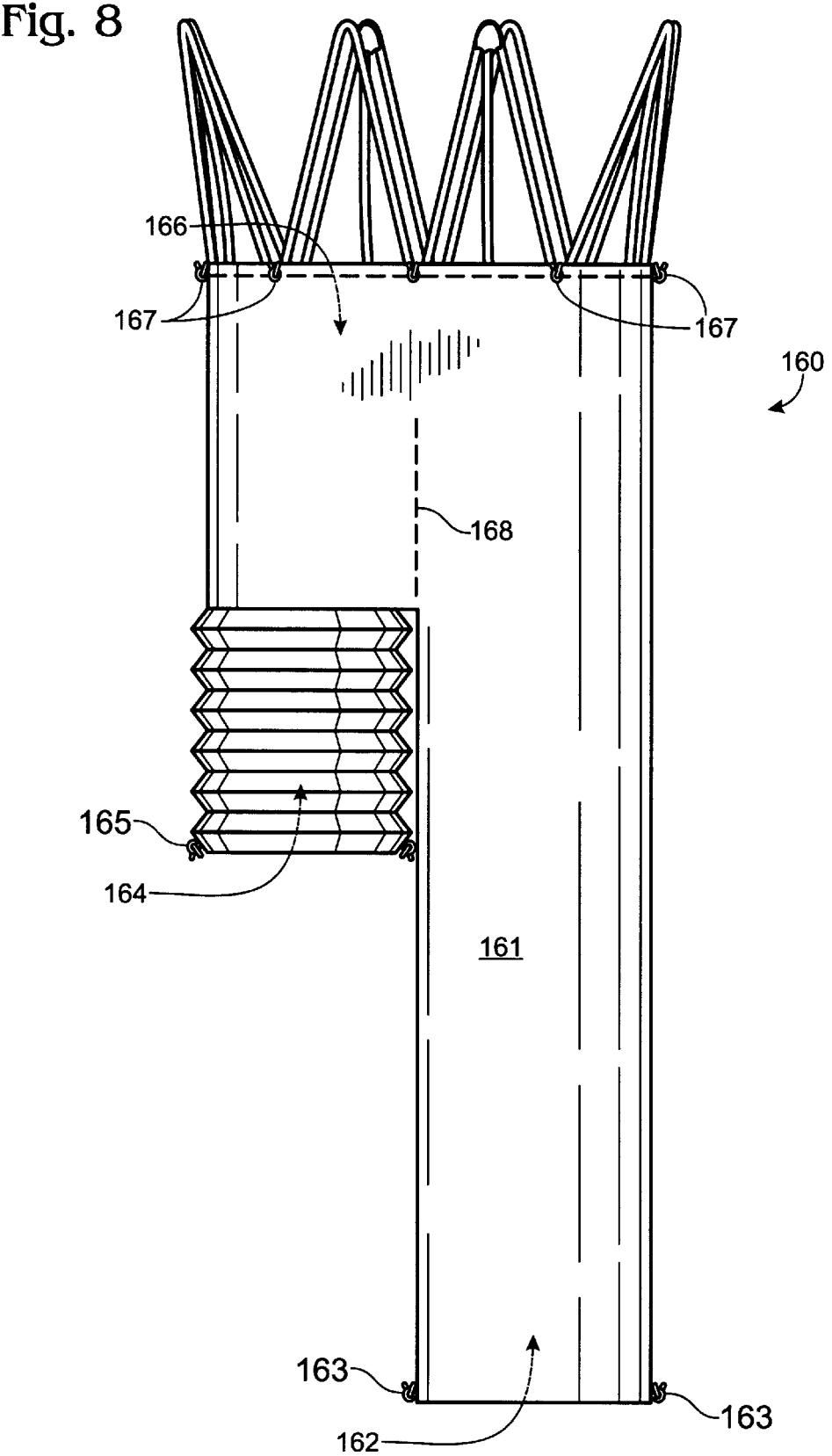
FIG. 8 is a plan view of the bifurcated stent of the FIG. 6 embodiment shown with tubular graft material attached thereto.

FIG. 8 illustrates the bifurcated configuration employing the sliding strut configuration illustrated in FIGS. 6 and 7. In other respects, the bifurcated configuration of FIG. 8 is the same as the bifurcated configuration illustrated in FIG. 5, and identical components of the FIG. 8 configuration have the same reference numbers as those used in FIG. 5, but increased by 100.

In FIG. 8, the sliding strut 152/252 (not shown) is in the collapsed configuration shown in FIG. 6. That portion of graft 161 covering sliding strut 152/252 and stent 150 is collapsed, accordion style, since it must have a length long enough to accompany stent 150 (to which it is attached by sutures 165) as strut portion 252 is extended.

The endoskeletons of both the straight stent graft 30 and bifurcated stent graft 60 are easily compressed into a small diameter endoprosthesis package for percutaneous delivery to the required aneurysm repair site since a minimum number of stents are employed (two in straight stent graft 30 and three in stent graft 60). For example, straight stent graft 30 can be collapsed to a diameter of about 3.3 mm and bifurcated stent graft 60 can be collapsed to a diameter of about 4.0 mm.

The stent grafts 30 and 60 of the invention are introduced through a conventional sheath with a hemostatic valve. The sheath and taper dilator is initially positioned over an intravascular guide wire. The tapered dilator is removed and the stent graft is advanced through the sheath with a blunt pushing device. The distal tip of the sheath is demarcated with a radiopaque marker.

After stent graft 30 or stent graft 60 is secured in place in the artery of a patient, additional (secondary) stents can be inserted inside the graft tube along the length thereof.

What is claimed is:

1. A stent graft for the treatment of vascular abnormalities comprising:
    a first self-expandable stent;
    a second self-expandable stent, said second stent being spaced from said first stent;
    each of said first and second self-expandable stents including a plurality of arms and inner and outer elbows joining said arms to thereby form a sinusoidal configuration;
    at least one strut member having first and second outer ends, said strut member being attached at its first outer end to an outer elbow of said first stent and attached at its second outer end to an outer elbow of said second stent; and
    a tubular graft extending between said first and second stents.

2. The stent graft of claim 1 wherein there are at least three strut members, each having first and second outer ends, said strut members being attached at their first outer ends to individual outer elbows of said first stent and attached at their second outer ends to individual outer elbows of said second stent.

3. The stent graft of claim 1 wherein said first stent has a larger diameter than said second stent, said stent graft including a third self-expandable stent having a plurality of arms and inner and outer elbows joining said arms to thereby form a sinusoidal configuration, at least one secondary strut member extending between said first and third stents, said secondary strut member having first and second outer ends, said secondary strut member being attached at its first outer end to an outer elbow of said first stent and attached at its second outer end to an outer elbow of said third stent, said tubular graft being bifurcated with a portion thereof extending between said first and second stents and a portion thereof extending between said first and third stents.

4. The stent graft of claim 3 wherein said tubular graft is attached to inner elbows of said first stent.

5. The stent graft of claim 3 wherein there are at least three strut members extending between said first and second stents, each said strut member having first and second outer ends, said strut members being attached at their first outer ends to individual outer elbows of said first stent and attached at their second outer ends to individual outer elbows of said second stent.

6. The stent graft of claim 3 wherein said secondary strut member is comprised of two strut sections adapted to be slidable relative to each other from a first, collapsed position to a second, extended position, said portion of said tubular graft extending between said first and third stents being expandable to the length of said second strut member when in its second, extended position.

7. An endoskeleton for a stent graft used for the treatment of vascular abnormalities comprising:
   a first self-expandable stent;
   a second self-expandable stent, said second stent being spaced from said first stent;
   each of said first and second self-expandable stents including a plurality of arms and inner and outer elbows joining said arms to thereby form a sinusoidal configuration;
   at least one strut member having first and second outer ends, said strut member being attached at its first outer end to an outer elbow of said first stent and attached at its second outer end to an outer elbow of said second stent.

8. The endoskeleton of claim 7 wherein there are at least three strut members, each having first and second outer ends, said strut members being attached at their first outer ends to individual outer elbows of said first stent and attached at their second outer ends to individual outer elbows of said second stent.

9. The endoskeleton of claim 7 wherein said first stent has a larger diameter than said second stent, said endoskeleton including a third self-expandable stent having a plurality of arms and inner and outer elbows joining said arms to thereby form a sinusoidal configuration, at least one secondary strut member extending between said first and third stents, said secondary strut member having first and second outer ends, said secondary strut member being attached at its first outer end to an outer elbow of said first stent and attached at its second outer end to an outer elbow of said third stent.

10. The endoskeleton of claim 9 wherein there are at least three strut members extending between said first and second stents, each of said strut member having first and second outer ends, said strut members being attached at their first outer ends to individual outer elbows of said first stent and attached at their second outer ends to individual outer elbows of said second stent.

11. The endoskeleton of claim 9 wherein said at least one secondary strut member is comprised of two strut sections adapted to be slidable relative to each other from a first, collapsed position to a second, extended position.

* * * * *